United States Patent [19]

Sonnino

[11] 3,959,947

[45] June 1, 1976

[54] WINDING SUTURE REEL-LABELS

[75] Inventor: Mario Sonnino, New Canaan, Conn.

[73] Assignee: American Cyanamid Company, Stamford, Conn.

[22] Filed: Feb. 27, 1975

[21] Appl. No.: 553,392

Related U.S. Application Data

[63] Continuation-in-part of Ser. No. 386,672, Aug. 8, 1973, Pat. No. 3,876,068.

[52] U.S. Cl. .............................................. 53/21 FW
[51] Int. Cl.[2] ..................... B65B 25/00; B65B 63/04
[58] Field of Search ........................ 53/21 FW, 118; 206/63.3, 227; 242/222

[56] References Cited
UNITED STATES PATENTS

| | | | |
|---|---|---|---|
| 3,136,418 | 6/1964 | Stacy et al. | 206/63.3 |
| 3,180,487 | 4/1965 | Uddenborg | 206/227 |
| 3,357,550 | 12/1967 | Holmes et al. | 206/63.3 |
| 3,376,973 | 4/1968 | Granowitz et al. | 206/63.3 |
| 3,869,044 | 3/1975 | Olsson et al. | 206/63.3 |

*Primary Examiner*—Travis S. McGehee
*Assistant Examiner*—Horace M. Culver
*Attorney, Agent, or Firm*—Samuel Branch Walker

[57] ABSTRACT

Surgical sutures are wound from a needled end on a printed reel-label. The reel-label is made from sealed together thicknesses of stiff inert sterilizable label stock, with an aperture which acts as a rotable axis to permit holding between a finger and thumb for unwinding. The needle is held in a pocket between the thicknesses with the armed portions of the needle protected. The friction between the thicknesses and the suture permits retention of the suture during storage and unwinding from the needled end. The suture reel assembly is stored in a sterile envelope which may be completely dry. The package protects the suture from kinks during storage, and protects the suture from the needle and the package from the needle. It permits unwinding from either end without tangling.

3 Claims, 10 Drawing Figures

WINDING ON        WINDING OFF

WINDING ON

WINDING OFF

WINDING SUTURE REEL-LABELS

RELATED APPLICATIONS

This is a continuation-in-part of Ser. No. 386,672 filed Aug. 8, 1973, now U.S. Pat. No. 3,876,068, dated Apr. 8, 1975, SUTURE REEL-LABEL PACKAGE.

BACKGROUND OF THE INVENTION

In this modern day of convenience packaging, more and more effort is being put into attempting to package in a form which is convenient and economical and which meets requirements for the particular item being packaged.

In the packaging of surgical sutures, it is necessary that the sutures be released in sterile condition, ready for use by the surgeon with the economic requirement that the packaging be as economical as consistent with requirements.

An acceptable package needs to be inexpensive and completely reliable. The package must release a sterile suture for the surgeon's use with his positive knowledge that the suture is, in fact, sterile and none of its design characteristics have been compromised during storage prior to use. Sutures may be stored in hospitals for several years before use, although the usual storage time is much shorter.

There are many sizes of sutures, and many materials of construction, such as catgut, or polyglycolic acid for absorbables, and non-absorbables of silk, cotton, nylon, dacron, polyethylene, polypropylene, stainless steel, insulated stainless steel, and other materials of construction. There are several different needle types in common use, including pointed straight, pointed curved, three cornered straight, three cornered curved, both regular and reverse, and needles with side cutting edges of various types. The variations and combinations of each of these to meet the preferences of many surgeons for different operative procedures means that a suture manufacturer needs to supply different suture combinations running into the thousands. Some of these are fast moving items, others meet only with occasional demand. For purposes of convenience and storage in the hospital as well as economy of manufacture, it is highly desirable that as many suture combinations as feasible be packaged in a minimum number of different package styles and shapes and storage units. It is quite common to package three dozen identical sutures in a box. It is convenient to have most of the boxes about the same size and shape, so that the hospital may store them most conveniently. It is also convenient from the manufacturer's standpoint to be able to reduce his inventory of box sizes and to be able to use the same components for the maximum number of suture combinations in the product line.

It is essential that a package for a side cutting needle; that is, a needle which has a sharp edge on the side, protect the suture from contact with the sharp side, or armed edge, of the needle which could partially cut the suture and to avoid having the sharp edges cut the package. Also, the armed needle edges need to be protected so as to maintain their sharpness.

Additionally, it is highly desirable that the needles and sutures be oriented in a consistent relationship within packages so that the using surgeon, directly, or the nurse who passes the sutures to the surgeon, will be able to rapidly and reliably grip the needle without having to check orientation between packages of the same or different suture materials or needles.

Most of the suture packages today are strippable, double envelope packages of the type first disclosed in U.S. Pat. No. 3,043,067, Rynkiewicz and Ayres, "Suture Package", July 10, 1962.

The outer envelope and certain details are disclosed in U.S. Pat. No. 2,949,181, Buccino, "Suture Package And Process Of Making Same", Aug. 16, 1960.

U.S. Pat. No. 3,357,550, Holmes and Murphy, "Combination Reel And Label For Surgical Sutures", Dec. 12, 1967, shows a system in which the reel also serves as a label with the reel being torn apart to release the suture wound on the label.

U.S. Pat. No. 3,376,973, Granowitz and Buccino, "Package For Surgical Sutures", Apr. 9, 1968, shows a molded plastic reel fitting in a hub for surgical sutures with the assembled reel, hub and suture being packaged in outer envelopes.

U.S. Pat. No. 3,038,475, Orcutt, "Surgical Needles And Manufacture Of Same", June 12, 1962, shows certain forms of surgical needles, including curved, triangular shaped needles with the edges being sharp or round and which sharp side edges can damage sutures or packages.

U.S. Pat. No. 2,841,150, Riall, "Cutting Edge Suture Needle", July 1, 1958, shows another type of side cutting needle, the sharp edges of which can damage sutures or packages.

SUMMARY OF THE INVENTION

It has now been found that a suture package meeting the requirements set forth above is advantageously formed from sheet label stock one side of which is coated with a thermoplastic adhesive, such as polyethylene, with either a single sheet of such a material being doubled on itself to provide two thicknesses, or two separate sheets of material being sealed together and appropriately folded, so that the suture is wrapped between at least two thicknesses of the label stock which are sealed together. The suture is retained between the two sheets of material sealed together, whereby the suture is held in position until time for use and the suture is readily unreeled from either end from between the two thicknesses of label stock.

The needled end is placed on the reel-label first, and the free end is wound around the reel-label.

At the time of use, the needle is pulled free first and the suture is unwound from the needled end with the various turns of the suture passing each other in the V-groove between the label stock thicknesses, without tangling and without compromise of suture quality. Two or more needled sutures can be simultaneously wound and unwound.

An additional thickness of label stock, which may be transparent, covers and protects the needle from contact with either the turns of the suture or the envelope.

The needle is inserted in a retaining slit in the reel-label. The additional thickness of label stock covers the needle in such fashion that the needle protective cover can be turned back to release the needle in oriented relationship so that it may be picked up by the user in consistent orientation. Any of the usual types of needle forceps may be used.

The reel-label having the suture wound thereon may be packaged dry or in a selected tubing fluid in an interiorly and exteriorly sterile inner envelope, which inner envelope is packaged in a strippable outer envelope.

As is conventional in the art, the suture is served to a surgeon by stripping the outer envelope, and either with forceps, or by manually projecting, the inner envelope is passed across the sterile barrier, into the sterile areas of the operating room.

The inner envelope is opened at time of use.

Conveniently, the needles are of the eyeless type, that is permanently attached to the end of the suture and designed for but a single use. Such needles cause less trauma to tissues in which they are used and are becoming surgically preferred.

The present invention is particularly adapted for the packaging of polyglycolic acid sutures. These are a new class of synthetic absorbable suture which is to be packed and stored dry. The requirement for dryness is disclosed in U.S. Pat. No. 3,728,839, Glick, "Storage Stable Surgically Absorbable Polyglycolic Acid Products", Apr. 24, 1973.

The sutures may be of collagen, either natural catgut or regencrated catgut, which sutures are usually packed in a conditioning fluid such as a mixture of one or more alcohols in water so that the collagen will have a preferred flexibility. Non-absorbable sutures may be packed on the present reel-label and include such materials as silk, silicone or wax coated, or cotton or linen, or one of the newer synthetic materials such as nylon, polyester, isotactic polypropylene, or linear polyethylene, stainless steel wire or other wire, either insulated or bare, or the suture may be of such other composition as preferred by the surgeon.

The reel-label is preferably of a label paper which is manufactured for suture labels and is a sterilizable paper designed for either letter press or offset printing. A paper with a 90 lb. weight basis and designed to withstand heat, steam, or gas sterilization without discoloraion, and which accepts alcohol and water insoluble ink is satisfactory. It is preferred that such paper be coated with about ½ mil of polyethylene so that it becomes heat sealable. Such paper is known in the trade and readily available. The sealing may be by heated dies, or heat may be internally generated by ultrasonic means.

Time and motion studies show that the serving of a suture using the present reel-label is faster and more efficient than with conventional reels. Saving time reduces the time a patient is in surgery, and, hence, the duration of surgical risk, saves time of the medical operating team, and reduces time charges for the operating-theater, all of which are conducive to better and more economical patient care.

The present reel-label can have size and type designations for the suture and needle. The reel itself as well as the envelopes and boxes used may be color coded to designate the type of suture material, and/or other useful information.

The present invention, and its advantages are also apparent from the detailed description of certain embodiments thereof which follow.

THE DRAWINGS

Figure 1:
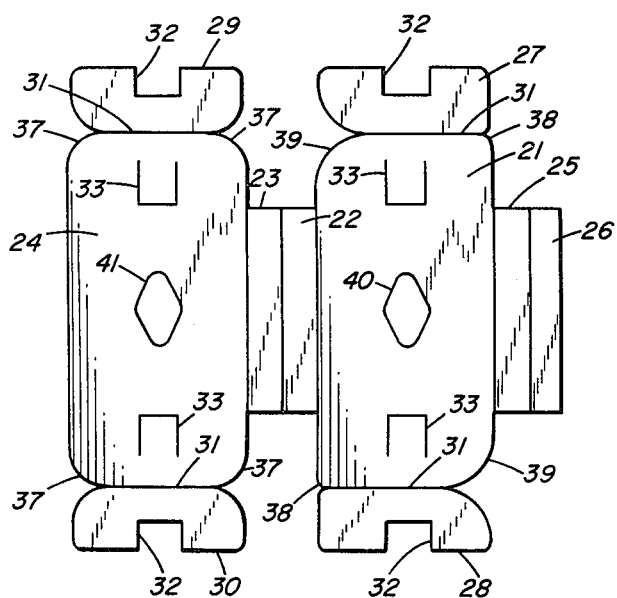
FIG. 1 shows a flat scored cut-out for a rectangular reel-label.

As shown in FIG. 1, a reel-label is cut out and scored from a sheet of stiff material such as 90 pound, sterilizable offset printing paper which has thereon a coating of ½ mil polyethylene so that it is heat sealable. The label is conveniently, but not necessarily, die cut from rolls of paper stock and conveniently may be cut out and printed in continuous rolls, except for a final cut which is made at the time the label is folded and sealed.

As shown in FIG. 1, with the printed side up and the polyethylene coated side down, face panel 21 has attached thereto along score lines first and a second accordion pleat panels 22 and 23, to the second of which is attached the back panel 24. On the other side of the rectangular panel are the third and fourth accordion pleat panels 25 and 26. Conveniently, but not necessarily, the third accordion pleat panel 25 is just slightly wider than the fourth accordion pleat panel 26 so that, in folding, when adhesively united to the back panel, the edge of the fourth accordion pleat panel is just slightly back of the edge of the back panel to insure that no edges stick out which can snag a suture being wound on the reel-label. Conveniently, when the reel-label is being cut, score lines are formed where the panels are to bend to insure that the bending occurs at a designed fold line.

To the top and bottom of the face panel and the back panel are attached ears, respectively, the top face panel ear 27, the bottom face panel ear 28, top back panel ear 29, and the bottom back panel ear 30. These ears are attached to the respective panels with score lines 31 being stamped into the label stock at the time of cut-out. These score lines permit accurately positioned folds to be readily made between the panels. A tab notch 32 is formed in each of the four ears. A tab 33 is cut on three sides near the top and bottom of each of the face and back panels pointing towards the center of the panels.

Figure 3:
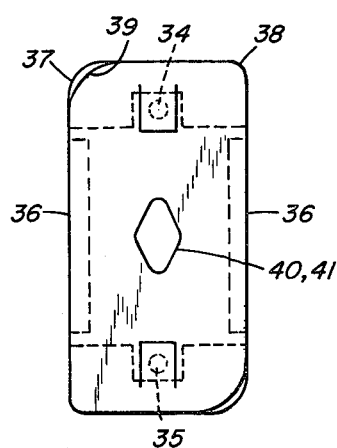
FIG. 3 is the cut-out of FIG. 1 folded, and sealed to itself as a reel-label.
Figure 2:
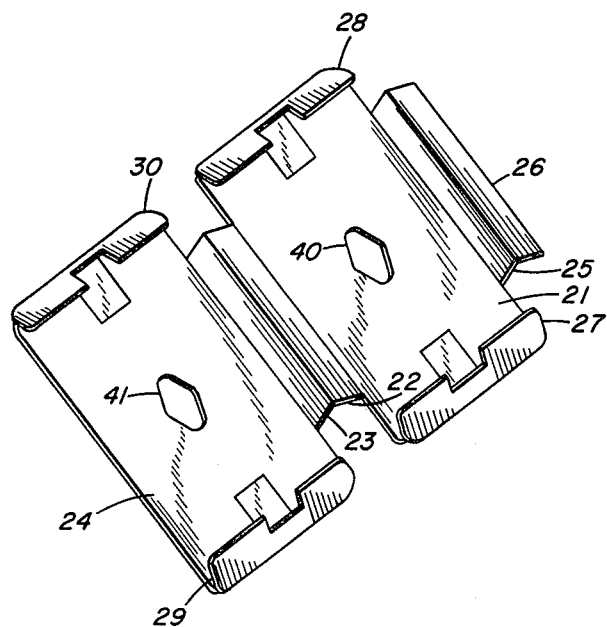
FIG. 2 is a pictorial view of the cut-out of FIG. 1 partially folded.
Figure 4:
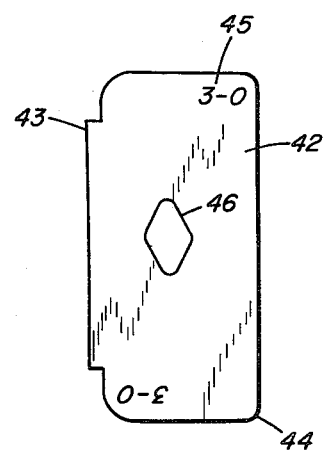
FIG. 4 is a needle protective cover for the reel-label of FIG. 3.

As shown in FIG. 2, the four ears are folded inwardly against the face and back panels with the adhesive coated sides coming into the contact and similarly the accordion pleat panels are folded inwardly from each panel so that the face and back panels can then be folded towards each other, as shown in FIG. 3, with the adhesive of the face and back panels being sealed to each other at the tabs, through the tab notches 32, in the upper tab seal zone 34 and the lower tab seal zone 35. This holds the face and back panels together in resilient spring-like configuration. The face and back panels are united with side seal zones 36 on each side which adhesively unite the accordion pleat panels to the face and back panels for the length of the accordion pleat panels and adhesively unite the panel ears to the respective panels. The seals may be formed consecutively or concurrently.

The ears are advantageously fractionally smaller than the face and back panel to which they are adhesively united. Conveniently, they may be about a 64th of an inch narrower, so that allowing for manufacturing tolerances in cutting and folding the ears, the ears are necessarily slightly back from the face and back panels so that no corners protrude on which the suture can be snagged. The corners may be slightly rounded to reduce the chance of snagging.

The back panel has four intermediate radius rounded corners 37. The face panel has diagonally oriented two smaller radius rounded corners 38 and two diagonal larger radius rounded corners 39. By having the larger and smaller radii on the front face, as the reel-label is assembled, two corners have the face panel protruding slightly beyond the back panel so that they may be lifted easily with the finger and the other two corners with a larger radius and, hence, are slightly back of the back panel so that on each of the corners, one of the panels may be conveniently manipulated to open up the winding notch 49 between the panels.

Near the center of the face panel is a face panel rotating hole 40 and near the center of the back panel is a back panel rotating hole 41. These holes extend through the panel so that in unwrapping the suture, the surgeon may hold the reel-label with the thumb and a finger on each side and touching through the hole to permit the reel-label to rotate during release of the suture. Preferably, the rotating hole is of a rounded polygon configuration. As shown, it is conveniently a diamond shaped hole with rounded corners. By having the hole other than round, the suture reel-labels may be mounted on a spindle and positively driven by a non-round spindle which is shaped to match the rotating hole. Conveniently, a diamond shaped hole with rounded corners is used, but a hexagonal, triangular, or other shaped hole may be used for the purpose if desired.

Figure 5:
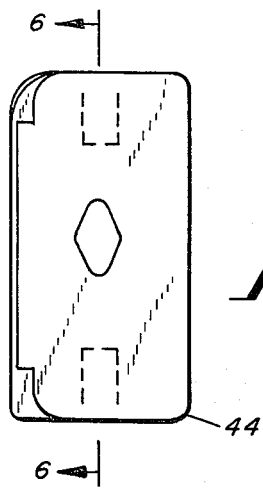
FIG. 5 shows a rectangular reel-label with needle protective cover.
Figure 6:
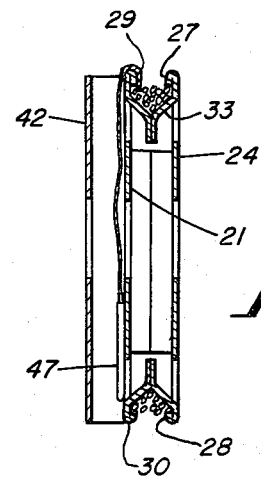
FIG. 6 is a cross-section of FIG. 5 at 6—6.

A separate needle protective cover 42 is cut from similar stiff label paper of a size and shape to nearly cover the face of the assembled panels with a cover seal flap 43. The needle protective cover is sealed along one edge to position the cover seal flap close to the face panel of the reel-label assembly, as shown in FIG. 5. One corner of the needle protective cover is a lifting corner 44 which extends slightly beyond the face panel so that it may be lifted by the thumb of the user.

Identifying indicia 45 may be printed on the needle protective cover. Conveniently, but not necessarily, a cover rotating hole 46 is formed in the needle protective cover so that the cover may be either in the closed position or in the open position as the reel-label is rotated to unwind a suture.

The needle protective cover may also be of a transparent material, for example, a mylar polyethylene laminate which permits inspection of the needle and suture while protecting the needle and suture. If transparent, the identifying indicia may either be printed on the needle protective cover or on the face panel of the reel-label.

More than one needled suture may be wound on a single reel-label.

Figure 7:
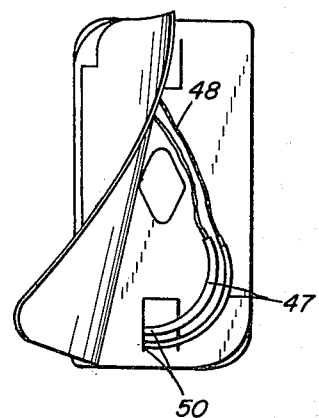
FIG. 7 shows the cover turned back to expose a curved needle and suture wound on the reel-label.

In FIG. 7 are shown two curved needles 47 which are inserted through the cut-out notch of the tab 33 so that the needles extend between the tab and the panel ear. This keeps the needles away from the suture and holds them in a positively oriented position until time of use. The sutures 48 extend from the curved needles 47 and are wound up and into the winding notch 49 which winding notch is formed by the tabs sealed together in the tab seal zones at the top and bottom and the accordion pleated panels on the edges. The sutures may be wound in this winding notch by wrapping the sutures in either direction with the free ends being wound down into the notch or left free. At the time of use, the needles may be removed from their pocket and unwound with the turns of the sutures passing each other in the winding notch. The number of sutures wound on a single reel-label may be adapted to meet requirements for a surgical procedure. Usually not more than three will be wound and unwound together.

By having the sutures fit in the winding notch 49 in such fashion that turns can pass each other, the suture may be wound or unwound from either end at any time. This permits placing the needle 47 first, and winding the suture in the winding notch without slack and yet without tension. The needle pocket 50, which is formed by the cut-out for the tab 33 and the panel ear, permits a needle to be placed between two thicknesses of the panel stock and out of contact with the suture independently of whether the needle is curved, straight, triangular in cross-section, or duck-billed with sharp sides, the needle pocket provides a receptacle in which the point may be placed and the diagonal from the pocket is long enough for the entire needle to be placed between the face panel and the needle protective cover 42.

If the tabs 33 are narrower than the tab notches, the reel-label is easier to assemble and has more resiliency. If the tab is slightly wider, the needle is necessarily more certainly diverted from passing into the winding notch rather than being retained between the face panel and the face panel ear.

For those packages in which the suture is double-armed, that is, has a needle on each end, a pocket at the top and a pocket at the bottom can be used, one for each needle. Alternatively, both needles may be placed in the same pocket.

Figure 8:
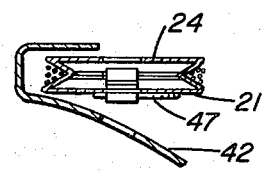
FIG. 8 is a cross-section of label-reel, having a suture wound thereon, and a separate needle protective cover.

In FIG. 8 is shown the suture wound between the accordion pleat panels. In this, as in other figures, the thickness of the panel stock is exaggerated for clarity.

In this embodiment the needle protective cover is a folded flap 52 which is placed over the needle to protect the needle, suture, and enclosing envelope from each other. The folded flap may be left in the inner envelope in which the suture reel-label assembly is stored at the time the suture is to be removed to be served to the using surgeon.

The niceties of having the radii of curvature on the face panel and the back panel different in each corner and having all corners slightly rounded, and slightly smaller so that even with manufacturing tolerances, none of the ears or accordion panels stick out enough to snag the suture are features which are preferred for the best practice of the invention. For many purposes, a less refined reel-label may be adequate.

The cover 42, as well as the paper stock from which the panels are formed, may be colored in order that the color of the reel-label gives a clue as to the type of suture material wound around. Similarly, the suture size, the suture material, and the type of needle may be printed on the needle protective cover on the face panel or the back panel. Usually, to avoid confusion, a minimum of printing is desirable in order that the user may very rapidly identify the data which is needed and not be too confused with extraneous information.

The size of the reel-label is, of course, commensurate with the size of the suture and its needle. Conveniently, a face panel which is 2 7/16 inches long and 1¼ inches wide gives good results. The radii of curvature of the back panel can conveniently be about a quarter of an inch whereas the smaller radius can be 1/16 inch and the larger radius ⅜ inch on the face panel with the ears 1/64 inch less on each corner. The accordion folds are conveniently a quarter of an inch for the first and second accordion pleat and a 1/64 of an inch more for the third accordion pleat panel and a 1/64 of an inch less for the fourth accordion pleat panel. Such a size permits sutures normally in use in a hospital to be conveniently packaged. For metric countries or where desired, panels may be varied considerably in size to accommodate sutures of selected sizes and appropriate needles.

Figure 9:
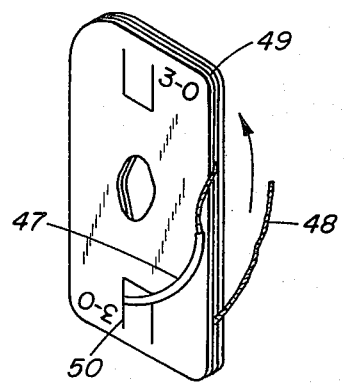
FIG. 9 shows a needle suture being wound on a reel-label with the needed end being attached first.

In FIG. 9 the needle 47 is shown engaged in the needle pocket 50 as the suture 48 is wound about the reel-label into the winding notch, or suture holding groove 49.

This suture holding groove 49 is sufficiently resilient to hold the successive turns of the suture in place without deformation, and to permit the turns to pass each other so that the free end is wound on last, and also wound off last. As the turns pass in the groove, snarling is effectively eliminated.

Winding the needle off first is highly desirable as, in use, needle forceps are used to hold the needle, and the suture is wound off from the needled end.

With most loading procedures, the suture is wound in the inverse of the method of unwinding — which raises problems of location of the needle. Here, the needle is emplaced first in winding, and the location of the free end is not material.

The ability of the present reel-label to permit winding on and winding off in either direction, and most conveniently with the needled end first, permits savings in time and effort in the packaging of the sutures.

Figure 10:
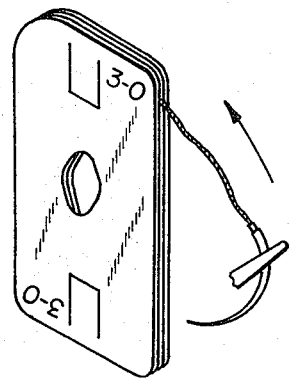
FIG. 10 shows a needle suture being wound off a reel-label with the needled end being wound off first, and the turns passing each other.

FIG. 10 shows the winding off of the suture with the needled end being released first.

Many incidental advantages accrue from the use of the present reel-label. For instance, it takes from 8 to 16 turns, depending on length, to wind a suture onto the present reel-labels. It is convenient to have one or more suture reel-labels ganged on a single spindle with the needles being inserted into the needle pockets. All of the sutures are wound on the reels by mechanically turned spindles simultaneously. Gang winding permits saving of time and effort, even though winding eight turns by hand is comparatively quick.

The use of rectangular reels gives a larger printing surface for identification of the suture type, size, and needle. Additionally, it provides a longer diagonal so that long straight needles can be inserted in the pocket and protected for their entire length. A rectangular reel permits the use of a rectangular envelope which maintains the orientation so that the user can expect to find a needle in the same relative position with respect to the envelope each time the sterile inner envelope is opened. This permits more rapid seizing of the needle with needle forceps with positive knowledge that orientation is as planned.

By having no sharp corners around which the suture is wound, even sutures which tend to attain a permanent set are curved minimally when unreeled for use.

By using the cover and having the needle point between the face panel and a face panel ear, the needle is positively positioned and is protected during winding so that the needle neither harms the suture nor the envelope nor has its sharpness compromised during the assembly and storage prior to actual use. The light frictional crimp from the sealed together panels permits as many as three sutures to be wound on a single reel and unwound without tangling.

I claim:
1. A method of loading and unloading a reel-label surgical suture combination,
   in which the reel-label has:
   two superimposed panels of stiff sterilizable label stock having a heat sealable facing on one side;
   said panels being rectangular, with rounded corners, with the superimposed rounded corners having different radii;
   accordion pleat folds joining the two panels on two parallel edges;
   an infolded panel ear strengthening the top and bottom of each said panel;
   cut-out tabs near the top and bottom of each panel, said tabs being heat sealed to tabs from the opposing panel, to hold said panels together;
   said panels each having therein a hole, said holes being in registration, and forming a spin axis substantially at the center of said panels;
   said tabs and said accordion pleat folds forming a suture holding groove, to frictionally hold a suture therein;
   said groove being effectively continuous and operatively centered towards said spin axis;
   at least one of said panels having therein at least one needle retaining cut-out adapted to hold the sharp end of at least one needle between panels in protective relationship;
   comprising inserting a surgical needle attached to a suture into a needle retaining cut-out, and winding the suture in friction holding relationship into a suture holding groove around the periphery of said reel-label, with the free end being wound onto said reel-label last;
   retaining the suture in the groove by friction of the pleats against the suture during shipment and storage;
   and on serving at time of use, under sterile conditions, removing said needle first, and then unwinding the suture with the initial windings passing the later windings in said suture holding groove while retaining said later windings by friction in said groove, so that the free end is released from frictional retention in said suture holding groove in said reel-label last.

2. The method of claim 1 comprising in addition the step of emplacing a needle protective cover over the surgical needle to protect the needle from dulling during shipment and to protect the suture and the package from being damaged by the needle during packaging and shipment, and holding the reel-label between the thumb and finger through the holes forming a spin axis, and rotating the reel-label while unwinding the suture.

3. The method of claim 1 in which at least two needled sutures are wound simultaneously on the reel-label, and later unwound simultaneously.

* * * * *